(12) United States Patent
Schmidt et al.

(10) Patent No.: US 6,297,017 B1
(45) Date of Patent: Oct. 2, 2001

US006297017B1

(54) CATEGORISING NUCLEIC ACIDS

(75) Inventors: Günter Schmidt, Houghton; Andrew Hugin Thompson, Ayr, both of (GB)

(73) Assignee: Brax Group Limited, Cambridge (GB)

( * ) Notice: Subject to any disclaimer, the term of this patent is extended or adjusted under 35 U.S.C. 154(b) by 0 days.

(21) Appl. No.: 09/462,636

(22) PCT Filed: Jul. 13, 1998

(86) PCT No.: PCT/GB98/02045

§ 371 Date: Apr. 10, 2000

§ 102(e) Date: Apr. 10, 2000

(87) PCT Pub. No.: WO99/02727

PCT Pub. Date: Jan. 21, 1999

(30) Foreign Application Priority Data

Jul. 11, 1997 (GB) .................................................. 9714716

(51) Int. Cl.[7] .............................. C12Q 1/68; C07H 21/00; C07H 21/02; C07H 21/04
(52) U.S. Cl. ................................................. 435/6; 536/25.3
(58) Field of Search ................................ 435/6; 536/25.3

(56) References Cited

U.S. PATENT DOCUMENTS

| | | | |
|---|---|---|---|
| 4,705,616 | * 11/1987 | Andersen et al. | 204/299 |
| 5,003,059 | * 3/1991 | Brennan | 536/27 |
| 5,508,169 | 4/1996 | Deugau et al. | 435/6 |
| 5,919,626 | * 7/1999 | Shi et al. | 435/6 |

FOREIGN PATENT DOCUMENTS

| | | |
|---|---|---|
| 0 667 393 | 8/1995 | (EP) . |
| 735144A1 | 10/1996 | (EP) . |
| WO 93/23562 | 11/1993 | (WO) . |
| WO 94/01582 | 1/1994 | (WO) . |
| WO 95/04160 | 2/1995 | (WO) . |

OTHER PUBLICATIONS

Kato, Nucleic Acids Research, vol. 23, No. 18, 1995, May 11, 19991, pp. 2251–2259, XP000204316.
Wong et al., Nucleic Acids Research, vol. 19, No. 9, May 11, 1991, pp. 2251–2259, XP000204316.
Guilfoyle et al., Nucleic Acids Research, vol. 25, No. 9, May 1, 1997, pp. 1854–1858, XP002076198.
Kato, Nucleic Acids Research, vol. 23, No. 18, 1995, pp. 3685–3690, XP–002053720.

* cited by examiner

*Primary Examiner*—Kenneth R. Horlick
*Assistant Examiner*—Teresa Strzelecka
(74) *Attorney, Agent, or Firm*—Burns, Doane, Swecker & Mathis, L.L.P.

(57) ABSTRACT

The present invention concerns a method for characterizing one or more nucleic acids. This method involves immobilizing double-stranded nucleic acids on a solid phase support and cleaving the immobilized nucleic acids with an endonuclease, such that each cleaved nucleic acid has a double-stranded portion. The cleaved nucleic acids are then denatured to form single-stranded cleaved nucleic acids. One or more oligonucleotide sequences are then hybridized to the resulting single-stranded cleaved nucleic acid. The oligonucleotide sequences used each comprise a predetermined recognition sequence situated such that it recognizes a sequence which was part of the double-stranded portion of the nucleic acid and a label specific to the recognition sequence. The hybridized oligonucleotide sequences are then extended along the single-stranded portion of the immobilized nucleic acid to form an extended strand which is then denatured from the immobilized strand. The immobilized nucleic acid is then characterized by identifying the size of the extended strand and the identity of the recognition sequence.

20 Claims, 2 Drawing Sheets

CATEGORISING NUCLEIC ACIDS

Figure 1A:
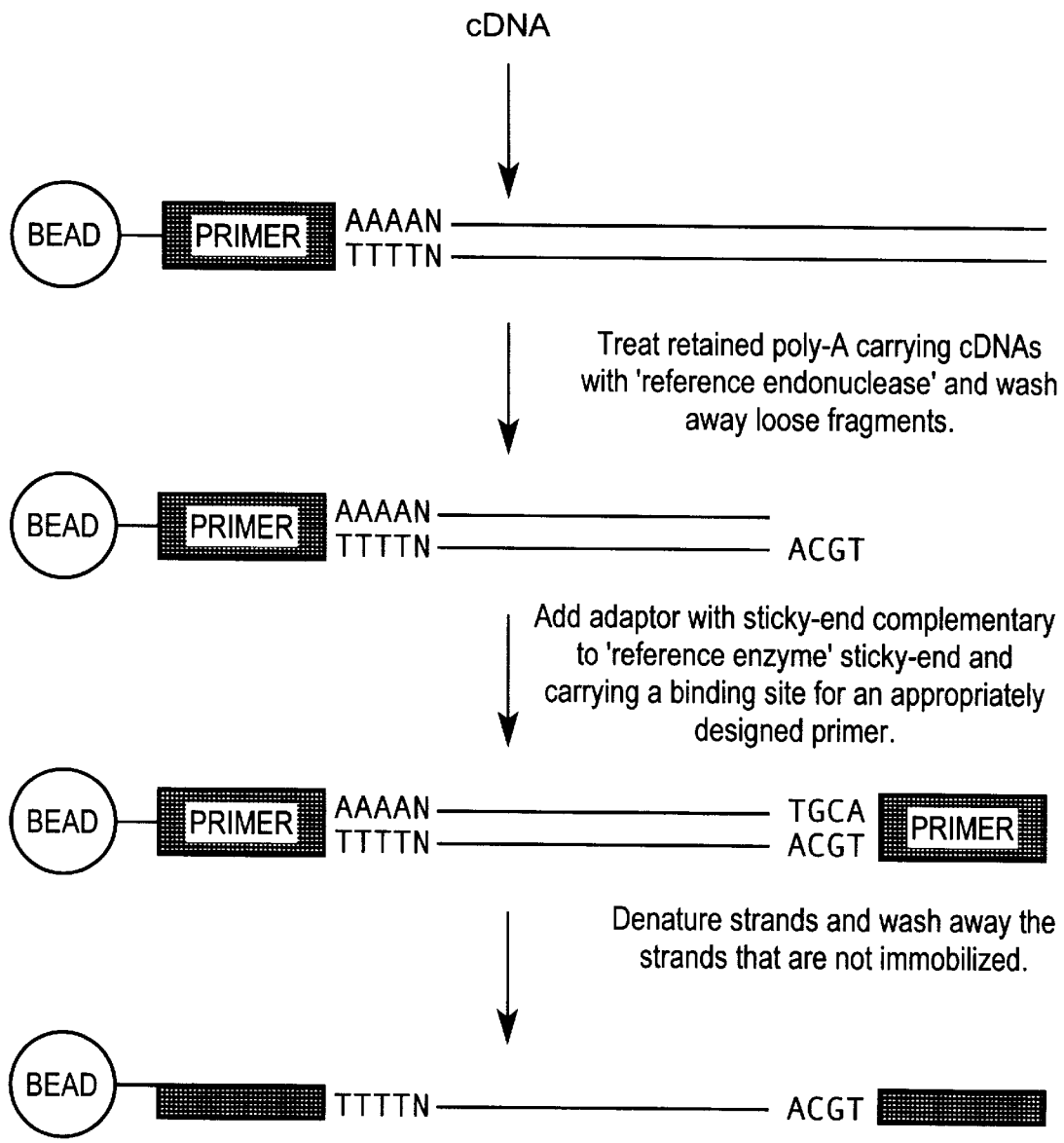

This invention relates to methods of analysing heterogeneous populations of nucleic acids. More specifically this application relates to improved methods of analysing populations of complementary DNA derived from polyadenylated messenger RNA.

Present methods suffer from numerous drawbacks. The simplest methods such as 'subtractive cloning' allow crude comparative information about differences in gene expression between related cell types to be derived, although these methods have had moderate success in isolating rare cDNAs, they are not suited to high throughput applications where large numbers of samples need to be analysed at low cost whilst still generating detailed data on the expression of a large number of genes, if not all genes simultaneously. Other methods such as 'differential display' and related 'molecular indexing' methods such as Sibson (PCT/GB93/0145) or Kato (EP 0 735 144 A1) allow generation of gene expression data for large numbers of genes in a single experiment but embodiments of these methods to data have not been fully automated and are dependant on gel electrophoresis for analysis. These methods are thus too labourious and expensive for high throughput applications. Still more informative methods have arrived recently such as SAGE, Serial Analysis of Gene Expression, which give quantitative data on gene expression without prior knowledge and can readily and specifically identify cDNAs expressed in a given cell type but at the cost of excessive sequencing for a high resolution gene expression profile.

Sibson, D. R., PCT/GB93/01452 provides methods for gene expression analysis using populations of adapter molecules to identify the ambiguous sticky-ends generated by cleavage of a nucleic acid with a type IIs restriction endonuclease to categories the cleavage fragments. Using specifically engineered adapters one can specifically immobilise or amplify or clone specific subsets of fragments in a manner similar to differential display but achieving a greater degree of sorting and control. The methods disclosed in this patent are difficult and expensive to automate.

Kato, Nucleic Acids Research 23, 3685–3690, 1995 and EP 0 735 144 A1 provides a method for analysing patterns of gene expression in a tissue which comprise sorting terminal cDNA fragments into sub-populations followed by selective amplification of specific subsets of cDNA fragments. Sorting is effected by using type IIs restriction endonucleases and adapters. The adapters also carry primer sites which in conjunction with general poly-T primers allow selective amplification of terminal cDNA fragments as in differential display. It is possibly more precise than differential display in that it effects greater sorting; only about 100 cDNAs will be present in a given subset and sorting can be related to specific sequence features rather than using primers chosen by trial and error. The subsets can then be analysed by gel electrophoresis to separate the fragments by length and generate a profile of mRNAs in a tissue. This method is dependant on PCR amplification which distorts the frequencies of each cDNA present. Furthermore the methods of analysis used so far have been dependant on gel electrophoresis.

The Gene Profiling technology described in patent PCT/GB97/02403 provides a further method of molecular indexing for the analysis of patterns of gene expression in a cell by sampling each cDNA within the population of that cell. In one embodiment, the sampling system takes two samples of 4 bp from each cDNA in a population and determines their sequence with respect to a defined reference point. The methods of this invention are amenable to automation but require many steps to derive signature information.

It is an object of this invention to provide a method of gene expression profiling that is amenable to high throughput and automation which has great sensitivity. In this way should be possible to avoid the need for exponential amplification of cDNAs which distorts the frequencies of the cDNAs which is essential information in interpreting changes in gene expression patterns between different states of a given tissue and between different tissues of the same organism which have differentiated differently. This invention provides methods to derive a signature for each cDNA in a library which require fewer steps than many conventional approaches hence reducing sample loss and distortion of measurements of quantities of each mRNA.

Accordingly, this invention provides a method for categorising one or more nucleic acids, which method comprises immobilising double-stranded nucleic acids on a solid phase support, cleaving the immobilised nucleic acids with an endonuclease such that each cleaved nucleic acid has a double-stranded portion, denaturing the cleaved nucleic acids to form single-stranded cleaved nucleic acid, hybridising one or more oligonucleotide sequences to the resulting single-stranded cleaved nucleic acid, each oligonucleotide sequence comprising a pre-determined recognition sequence situated such that it recognises a sequence which was part of the double-stranded portion of the nucleic acid and a label specific to the recognition sequence, extending correctly hybridised oligonucleotide sequences along the single-stranded portion of the immobilised nucleic acid to form an extended strand, denaturing the extended strand from the immobilised strand and characterising the immobilised nucleic acid by identifying the size of the extended strand and the identity of the recognition sequence.

This invention also provides a kit for categorising a nucleic acid, which kit comprises one or more adaptors and one or more sets of oligonucleotide sequences, wherein the adaptors comprise nucleic acid having a double-stranded primer portion of a known sequence and a single-stranded portion of a pre-determined length, either each single-stranded portion of each nucleic acid in the adaptors having the same pre-determined sequence or all possible sequences of the single-stranded portion being represented in the adaptors, and wherein each oligonucleotide sequence comprises a first sequence, a second sequence attached to the first sequence and a third sequence attached to the second sequence, in which the first sequence is complementary to the sequence of the primer portion of the adaptor, the second sequence is the same sequence as the single-stranded portion of the adaptors or all possible second sequences of the same length as the single-stranded portion of the adaptors are represented within the set of oligonucleotides, and the third sequence comprises a pre-determined recognition sequence.

Figure 1B:
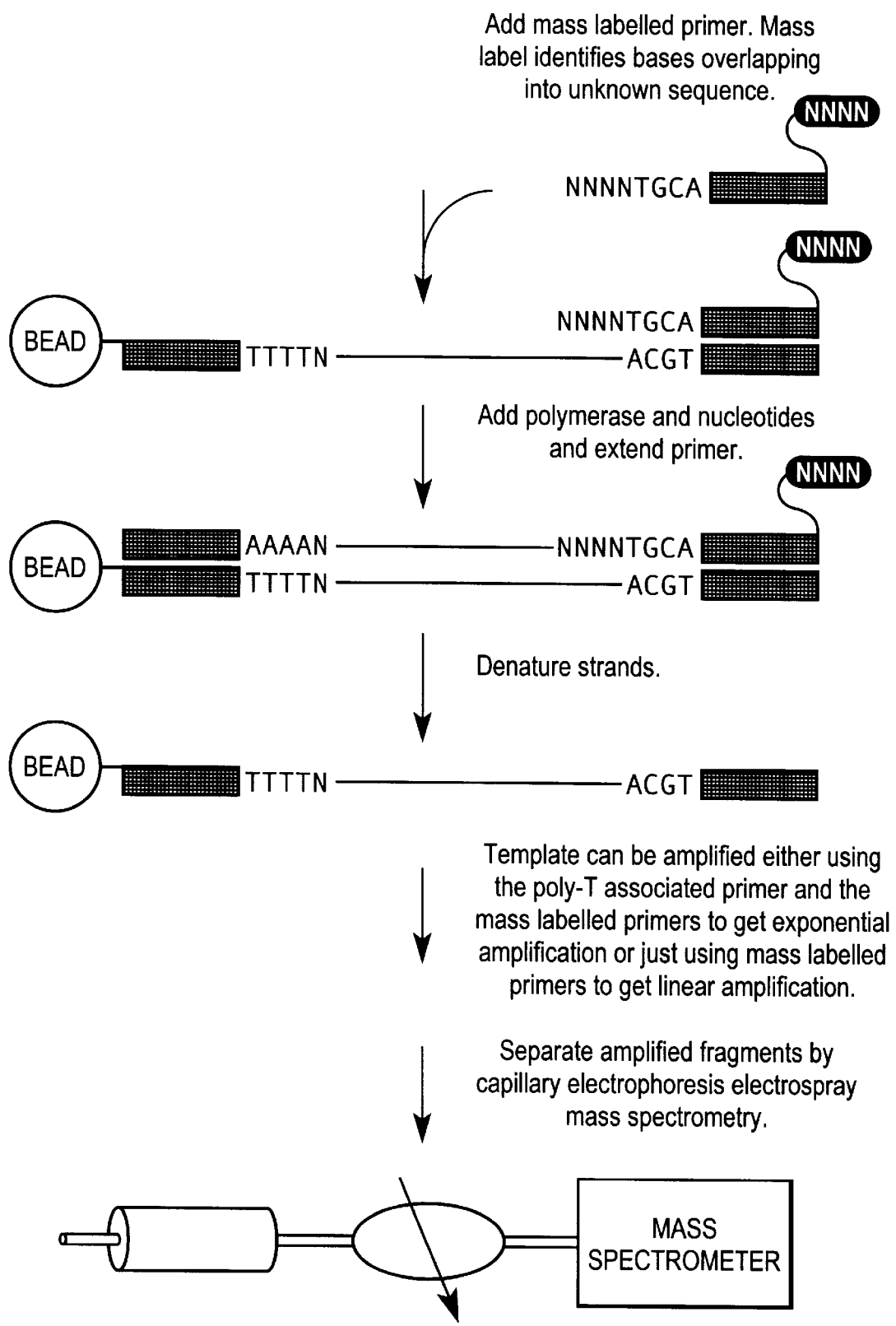

The invention will now be described in further detail by way of example only, with reference to the accompanying drawings, in which:

FIG. 1A shows a schematic of the steps of immobilising a cDNA, cleaving the cDNA, hybridising a primer to the cleaved cDNA, denaturing the cDNA and washing away non-immobilised species; and FIG. 1B shows a schematic of the steps of hydridising a labelled oligonucleotide sequence to the cleaved cDNA, extending the correctly hybridised oligonucleotide probe along the single-stranded cDNA, denaturing the extended strand, optionally amplifying the amount of extended strand using the immobilised cDNA template and separating the amplified fragments according to size and identifying the labels of the oligonucleotide sequences.

In a preferred embodiment, the method of this invention comprises the following steps:
1. Generating 'anchored' cDNA captured on a solid phase support at the poly-T terminus.
2. Cleaving the cDNA fragments with a type II restriction endonuclease, and washing away cleaved fragments. Preferably the type II restriction endonuclease generates a known sticky-end.
3. Ligating a double stranded adapter to the restricted cDNAs. Preferably the adapter bears a single stranded overlap complementary to a known sticky end generated by the restriction endonuclease from step (2) above. The adapter additionally comprises a predetermined sequence which can be used to as a primer sequence.
4. Denaturing the free strand from the captured strand releasing it into solution. The captured strands are thus rendered single stranded.
5. Optionally, washing away the released strands free in solution.
6. Contacting the captured single stranded fragments with mass labelled primers complementary to the primer sequence provided by the adapters and the known restriction site. The primers further comprise an additional sequence of a predetermined length which extends into the region of unknown sequence adjacent to the restriction site. The mass label attached to each primer identifies the sequence of the overlap of each primer. Primers are preferably non-complementary and have equalised melting temperatures and can thus be added simultaneously. Optionally a second primer or set of primers may be used. These may be the anchored primers used in the synthesis of cDNA or may be a primer complementary to a site provided 5' of the anchored poly-T sequence.
7. Extending primers in correctly hybridised duplexes with a DNA polymerase in the presence of nucleotide triphosphates. This may be an exponential amplification is a second primer or set of primers is used.
8. Melting the extended labelled strands off the immobilised template.
9. Optionally, conditioning the labelled cDNAs for mass spectrometry.
10. Determining the length of each of the amplified fragments and determining the identity of each of the amplified fragments by detection of the label incorporated with its primer. This detection if preferably performed by capillary electrophoresis mass spectrometry.

U.S. application Ser. No. 09/341,646 describes nucleic acid probes labelled with markers that are resolvable by mass spectrometry. Such mass labelled probes would permit the analysis described here to be performed very rapidly as a captured library of restriction fragments can be probed with a large number of uniquely mass labelled primers simultaneously.

Preparation of cDNA

The methods of this invention entail isolating a terminal restriction fragment from each cDNA in a library, from either the 3' or the 5' terminus, from which a short window of sequence is determined at a known location with respect to the terminal restriction site. In order to exploit fragment length information to categorise a cDNA population, the cDNA is prepared with 'anchored primers' which ensure that all cDNAs are terminated with a short poly-A tail of fixed length. In an 'anchored primer' cDNA preparation, poly-A carrying mRNAs are captured and primed using an oligonucleotide of about 18 deoxythymidine residues with one of the three remaining bases at the 3' end to anchor the primer at the end of the poly-A tract. The primed mRNA is then copied into DNA with reverse transcriptase. This generates an mRNA/DNA hybrid duplex. The complementary strand of DNA thus synthesised, can then be made double-stranded. Various methods are known in the art to effect the synthesis of the second strand. DNAse I can be used to nick the mRNA/DNA duplex providing 3' hydroxyls for a DNA polymerase to synthesise from. Alternatively the second strand synthesis may be effected using a second primer whose sequence is designed to bind within a coding sequence or is aimed at the 5' terminus of the complementary strand or which introduces a restriction site into the cDNA. This approach requires the degradation of the mRNA in the hybrid duplex. This may be effected by treatment with an alkali, by thermal denaturation or by treatment with RNAse H. A further method is the use of terminal transferase. If the 'anchored primer' is biotinylated, it can be captured onto an avidinated surface, or if it is already covalently linked to a solid phase substrate then after synthesis of the complementary strand the reverse transcriptase and nucleotides can be readily washed away. Buffer containing terminal transferase and one type of nucleotide triphosphate can then be added which will add an arbitrary number of nucleotides of that type to the 3' hydroxyls of the duplex. This generates a known sequence at the terminus of the cDNA, preferably poly-cytosine or poly-guanine. After removing the RNA, by thermal denaturation or alkali degradation, the reverse strand can be synthesised by providing an oligonucleotide primer complementary to the terminal transferase generated terminal sequence. This primer can additionally introduce a restriction site for an infrequently cutting endonuclease to permit the resultant cDNA library to be readily recombined with an appropriate vector to allow the cDNA library to be maintained in culture. Many other methods are known and any method that allows the generation of the complementary strand can be used with the methods of this invention but preferably the method chosen should not entail loss of any portion of the library.

In addition to normalising the length of the poly-A tail of each RNA species, the anchoring base on the poly-T primers can be used in the preparation of the cDNAs to sort the cDNA population into subsets. If a 1 base overlap is used cDNA population can be sorted into 3 subsets. With 2 bases 12 subsets are possible and similarly with a 3 base overlap 48 sets are possible. Preferably a 1 base overlap or a 3 base overlap is used. With a 1 base overlap, the mRNA extract from a tissue is subdivided into 3 pools and is contacted with one of the three possible anchoring primers in each pool separately from which cDNA is then reverse transcribed.

When the length of the poly-A tail is normalised as above it is possible to use the length of poly-A bearing terminal cDNA restriction fragments to categorise every cDNA in a population into restriction fragment length subset. With a short signature of about 4 bp from a known position within the fragments it should be possible to uniquely identify the majority of cDNAs in a population. Those cDNAs that are not uniquely resolved are likely to fall into gene families whose sequences are closely related.

To determine signatures from 'anchored' cDNAs according to the methods of this invention, each cDNA in a population is immobilised on a solid phase substrate. The cDNA is prepared as above by capturing the poly-A+ mRNAs with anchored poly-T primers, preferably with a single phase locking base at its 3' terminus. Additionally the anchored primers are biotinylated allowing the cDNAs to be immobilised onto an avidinated matrix. Alternatively the anchored primers can be covalently linked to the solid phase substrate. The phase locking base can be used to subdivide the sample into three separation populations for amplification if that is desired. The poly-T primer may additionally carry a primer sequence at its 5' terminus. The captured cDNAs generated are then cleaved with an ordinary type II restriction endonuclease. An adapter is ligated to the resulting known sticky-end. The adapter is designed to carry a primer sequence. The resulting double stranded construct is then denatured. The strand that is not immobilised can be washed away if desired. A family of primers complementary to the adapter primer with an overlap of 4 bases into the unknown sequence adjacent to the adapter primer, is added to the denatured mixture. With a 4 base overlap there are 256 possible primers. To identify the probes, they are tagged with mass labels using a cleavable linker, so that each of the 256 possible 4 bp overlaps is identified by a label that is uniquely identifiable in a mass spectrometer. These labels are optimised for good performance in a mass spectrometer as discussed in patent application U.S. application Ser. No. 09/341,646; The result of the application of the above procedure is a population of fragments each of which has a characteristic length, according to where the ordinary type II restriction endonuclease cut it, and one of 256 possible mass labelled primers hybridised at the cut site. The hybridised labelled primer is then extended by contacting the hybridisation complex with a DNA polymerase in the presence of deoxynucleotide triphosphates. The labelled polynucleotides thus generated are complementary to the library of fragments captured on the solid phase support. These double stranded nucleic acids may be denatured, thermally or otherwise and the free labelled strands may be analysed at this stage by Capillary Electrophoresis Mass Spectrometry.

In preferred embodiments the step of restriction of nucleic acids is coupled to the ligation of adapters (steps (2) and (3) in the description of the invention-above). Preferred restriction endonucleases for use with this invention cleave within their recognition sequence generating sticky-ends that do not encompass the whole recognition sequence. This allows adapters to be designed that bear sticky ends complementary to those generated by the preferred restriction endonuclease but which do not regenerate the recognition site of the preferred restriction endonuclease. This means that if the restriction reaction is performed in the presence of ligase and adapters, the ligation of restriction fragments to each other is reduced by continuous cleavage of these ligations whereas ligation of adapters is irreversible so the presence of adapters drives the restriction to completion and similarly the restriction endonuclease drives the ligation reaction to completion. This process ensures that a very high proportion of restriction fragments are ligated to adapters. This is advantageous as ligation of adapters to restriction fragments can be a relatively inefficient process. This is due to random ligation of restriction products to each other if these are phosphorylated.

In this embodiment the adapters used are preferably not phosphorylated at their 5' hydroxyl groups so that they cannot ligate to themselves.

In a preferred embodiment the steps of denaturing the single stranded captured cDNA restriction fragments and of contacting the resultant single stranded captured nucleic acids with labelled primers followed by primer extension can be performed as many times as desired. If only the adapter primer sites are used, a linear amplification can thus be performed. This causes smaller distortion of cDNA quantification than exponential amplification. If exponential amplification is desired then the poly-T oligos used to trap the mRNAs must carry a primer site as well. Exponential amplification may be desirable if small tissue samples must be analysed despite the potential for distortions of cDNA frequencies. Primers for generation of cDNAs from mRNA with amplification primer sites at the poly-A terminus of the cDNA have a formula as below:

3' OH-$N^3T_{15-23}$ [PRIMER]-[ADDITIONAL SEQUENCE]-Biotin

In the above primer $N^3$ indicates that one of Adenine, Cytosine or Guanidine are present at the 3' position in the primer. $T_{15-23}$ indicates that between fifteen and twenty-three thymidine residues follow the 3'-most base. These are then followed by an arbitrary primer sequence which is preferably between 18 and 23 bases in length. Additional sequence may comprise restriction sites to permit the cDNA library that is generated to be cloned. The 5' hydroxyl is shown as biotinylated above. The 5' hydroxyl may alternatively be covalently liked to a solid phase support or may be unlabeled if the library is to be recombined into a vector to permit the library to be maintained in culture. Growth of a library in culture represents a further form of amplification.

Mass spectrometry measures the mass/charge ratio of ions. Large organic molecules can enter multiple ionisation states and can also form adducts with a variety of solutes, particularly metal ions. This can result in significant 'noise' in the mass spectra generated for the labelled cDNAs eluting from a capillary electrophoresis column. It may be desirable to condition labelled cDNAs for mass spectrometry to ensure that the DNA is minimally ionised in the mass spectrometer. Electrospray Ionisation techniques are particularly sensitive to buffers and conditioning of analytes. Conditioning may be performed after synthesis of labelled cDNAs prior to denaturing the labelled complex. The captured strands may be washed in appropriate buffers which do not contain metal ions, at a pH which minimises the ionisation of DNA. Alternatively conditioning may take place after generation of labelled strands. These may be precipitated and resuspended in appropriate buffers.

The methods of this invention can exploit Liquid Chromatography Mass Spectrometry (LCMS), preferably capillary electrophoresis mass spectrometry. The gene profiling process operates in a two stage process, separation of restriction fragments by length followed by analysis of the mass labels ligated to the termini of the cDNA fragments. The separation by length could be achieved using capillary electrophoresis as the liquid chromatography stage feeding directly into an electrospray mass spectrometer. Between the capillary and the mass spectrometer the labels would have to pass through a cleavage stage to release all the mass labels from their restriction fragments. These features are discussed in PCT/GB98/00127. For each restriction fragment length band from the capillary electrophoresis separation, the quantity of each mass label present in that band is determined. This would subsort every group with a distinct fragment length into 256 subsets. If the phase locking base on the poly-T primers used in the preparation of the cDNAs is used to sort the cDNA population further then, the cDNA restriction fragments can be sorted into 768 subsets. Additional sub-sorting can be achieved using more than one base to lock the poly-T primer but the stringency of hybridisation is poorer the longer the probe sequence that is used.

To be able to uniquely identify each of the estimated, 100 000 genes in the human genome, one will need to be able to resolve cDNAs into at least as many subsets. For practical purposes unique resolution is not strictly necessary but resolution into a large number of subsets is desirable as it makes it more likely that a cDNA can be unambiguously identified by sorting alone. A combination of sorting a cDNA library followed by probing to generate a short sequence signature can allow an arbitrary degree of resolution of a cDNA library into subsets that are unique or nearly so. The signature can resolve a population into approximately 256 subsets if 4 base pair probe sequences are used at the adapter sites. The anchored primer can resolve cDNAs into further subsets. With a 1 base overlap the anchored primers can generate 3 subsets. This gives an initial total of 768 subsets. Restriction fragment lengths vary to a fairly wide degree giving further resolution that is statistically definable. Higher resolution could be achieved by using restriction enzymes that cut more rarely or by using combinations of enzymes. It might be desirable to perform two or more analyses per tissue using a different restriction endonuclease in each experiment to produce two or more sets of data for correlation.

Each such experiment will generate a signature of the form shown below for each cDNA in a population:

Adaptor Sequence-Restriction Site-Known Length-$N_w$-Measured Length-$N_x$-Poly-A tail (Known Length)-Optional Primer Sequence The features in bold are features of the source mRNA. N is base information where the subscripts w and x indicate the number of bases that are determined. The 'Measured Length' is determined by CEMS. The information generated comprises a digital signature that can be used to search a sequence database to identify the source gene.

Advantageously, if a signature does not match a gene in a gene database or if a signature matches more than one gene, the methods of this invention allow these genes to be identified or resolved. The methods of this invention preferably generate captured cDNAs which are used as templates for the synthesis of labelled strands whose length and label identify the source cDNA. These templates strands can be retained after generation of labelled complementary strands for further analysis. The signature provides a pair of primers which may be used to amplify unknown or ambiguous samples which can be sequenced directly if they are unknown or can be cloned and then sequenced if the signature is ambiguous.

What is claimed is:

1. A method for categorising one or more nucleic acids, which method comprises immobilising double-stranded nucleic acids on a solid phase support. Cleaving the immobilised nucleic acids with an endonuclease such that each cleaved nucleic acid has a double-stranded portion, denaturing the cleaved nucleic acids to form single-stranded cleaved nucleic acid, hybridising one or more oligonucleotide sequences to the resulting single-stranded cleaved nucleic acid, each oligonucleotide sequence comprising a pre-determined recognition sequence situated such that it recognises a sequence which was part of the portion of the nucleic acid which was double-stranded after cleavage with the endonuclease and a label specific to the recognition sequence, extending correctly hybridised oligonucleotide sequences along the single-stranded portion of the immobilised nucleic acid to form an extended strand, denaturing the extended strand from the immobilised strand and characterising the immobilised nucleic acid by identifying the size of the extended stand and the identity of the recognition sequence.

2. A method according to claim 1, wherein the nucleic acid is cDNA.

3. A method according to claim 1, wherein the endonuclease is selected such that each of the cleaved nucleic acids has a sticky end of known common length extending from the free terminal formed by the cleavage.

4. A method according to claim 3, wherein the endonuclease is selected such that each sticky end of each of the cleaved nucleic acids has the same known base sequence.

5. A method according to claim 4, wherein prior to contacting the cleaved nucleic acids with the oligonucleotide sequences, the nucleic acids are contacted with an adaptor to ligate the adaptor to the free terminal of each of the cleaved nucleic acids, wherein the adaptor comprises a double-stranded primer portion having a known base sequence, and a single-stranded portion complementary to the known sticky-end of the cleaved nucleic acids.

6. A method according to claim 5, wherein each oligonucleotide sequence comprises a first sequence, a second sequence attached to the first sequence and a third sequence attached to the second sequence, in which the first sequence is complementary to the sequence of the primer portion of the adaptor, the second sequence is complementary to the known sticky end of the cleaved nucleic acids, and the third sequence comprises the pre-determined recognition sequence.

7. A method according to claim 3, wherein the endonuclease is selected such that the sticky ends of the cleaved nucleic acids have a plurality of different base sequences.

8. A method according to claim 7, wherein prior to contacting the cleaved nucleic acids with the oligonucleotide sequences, the nucleic acids are contacted with an array of adaptors to ligate an adaptor to the free terminal of the cleaved nucleic acids, wherein each adaptor comprises a double-stranded primer portion having a known base sequence, and a single-stranded portion of the same length as the sticky ends of the cleaved nucleic acids, all of the possible base sequences of the single-stranded portion of the adaptor being represented in the array of adaptors.

9. A method according to claim 8, wherein each oligonucleotide sequence comprises a first sequence, a second sequence attached to the first sequence and a third sequence attached to the second sequence, in which the first sequence is complementary to the sequence of the primer portion of the adaptors, the second sequence is of the same length as the sticky ends of the cleaved nucleic acids, and the third sequence comprises the predetermined recognition sequence, and wherein in any one group of oligonucleotides having the same recognition sequence all of the possible base sequences of the second sequence are represented.

10. A method according to claim 1, wherein an array of oligonucleotide sequences is contacted with the cleaved nucleic acids, each of the oligonucleotides in the array having a recognition sequence of a common length, all possible recognition sequences of that length being represented in the array.

11. A method according to claim 1, wherein the recognition sequence comprises 4 bases.

12. A method according to claim 1, wherein the steps of hybridising the oligonucleotide sequences to the cleaved nucleic acids, extending correctly hybridised oligonucleotide sequences and denaturing the extended strand from the captured strand are repeated to linearly amplify the quantity of extended strands.

13. A method according to claim 1, wherein characterising the immobilised nucleic acid by identifying the extended strand and the identity of the recognition sequence is carried out by capillary electrophoresis mass spectrometry.

14. A method according to claim 1, wherein the oligonucleotide sequences have equalised melting temperatures.

15. A method according to claim 14, wherein the melting temperatures are equalised by incorporating one or more analogues of natural nucleotides into the oligonucleotide sequences, the analogues comprising base modifications, sugar modifications and/or backbone modifications.

16. A method according to claim 1, wherein the endonuclease is selected such that it cuts the nucleic acid at a site within the recognition site of the endonuclease.

17. A method according to claim 1, wherein the labels on the oligonucleotide sequences are mass labels.

18. A kit for categorising a nucleic acid, which kit comprises one or more adaptors and one or more sets of oligonucleotide sequences, wherein the adaptors comprise nucleic acid having a double-stranded primer portion of a known sequence and a single-stranded portion of a pre-determined length, either each single-stranded portion of each nucleic acid in the adaptors having the same pre-determined sequence or all possible sequences of the single-stranded portion being represented in the adaptors, and wherein each oligonucleotide sequence comprises a first sequence, a second sequence attached to the first sequence and a third sequence attached to the second sequence, in which the first sequence is complementary to the sequence of the primer portion of the adaptor, the second sequence is the same sequence as the single-stranded portion of the adaptors or all possible second sequences of the same length as the single-stranded portion of the adaptors are represented within the set of oligonucleotides, and the third sequence comprises a pre-determined recognition sequence.

19. A kit according to claim 18, wherein the recognition sequence comprises 4 bases.

20. A kit according to claim 18, additionally comprising an endonuclease.

* * * * *